US00PP17306P2

(12) United States Plant Patent
Olesen

(10) Patent No.: US PP17,306 P2
(45) Date of Patent: Dec. 26, 2006

(54) MINIATURE ROSE PLANT NAMED 'POULPAR038'

(50) Latin Name: ***Rosa* hybrid**
Varietal Denomination: Poulpar038

(75) Inventor: Mogens Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 1 day.

(21) Appl. No.: 11/266,618

(22) Filed: Nov. 4, 2005

(51) Int. Cl.
*A01H 5/00* (2006.01)

(52) U.S. Cl. ..... Plt./121

(58) Field of Classification Search ..... Plt./121
See application file for complete search history.

*Primary Examiner*—Kent Bell
*Assistant Examiner*—June Hwu

(57) ABSTRACT

A new miniature rose plant that has abundant, deep pink flowers and attractive foliage. The variety successfully propagates from softwood cuttings and is suitable for year-round production in commercial glasshouses. This new and distinct variety has shown to be uniform and stable in the resulting generations from asexual propagation.

1 Drawing Sheet

Botanical designation: *Rosa* hybrid.
Variety denomination: 'Poulpar038'.

SUMMARY OF THE INVENTION

The present invention constitutes a new and distinct variety of miniature rose plant which originated from a controlled crossing between the female seed parent, an unnamed seedling, and the male pollen parent an-unnamed seedling.

The two parents were crossed during the summer of 2002 and the resulting seeds were planted in a controlled environment in Fredensborg, Denmark. The new variety, named 'Poulpar038', originated as a single seedling from the stated cross.

The new variety may be distinguished from its female seed parent by the following combination of characteristics:

1. The seed parent is less compact in growth habit than 'Poulpar038'.
2. The seed parent has fewer flower petals than 'Poulpar038'.

The new variety may be distinguished from its male pollen parent by the following combination of characteristics:

1. Flowers of the pollen parent have more than 50 fower petals, while flowers of 'Poulpar038' have 35 to 40 flower petals.
2. Flowers of 'Poulpar038' are Red-Purple Group N57 B. The pollen parent has flowers which are Red Group 55 B.

The objective of the hybridization of this rose variety for commercial culture was to create a new and distinct variety with unique qualities, such as:

1. Uniform and abundant deep pink flowers that retain their color as flowers mature;
2. Vigorous and compact growth;
3. Year-round flowering under glasshouse conditions;
4. Suitability for production from softwood cuttings in pots;

5. Extremely durable flowers and foliage which make a variety suitable for distribution in the floral industry.

This combination of qualities is not present in previously available commercial cultivars of this type, known to the inventors, and distinguish 'Poulpar038' from all other varieties of which we are aware.

As part of the rose development program, Mogens N. Olesen germinated the seeds from the aforementioned hybridization and conducted evaluations on the resulting seedlings in a controlled environment in Fredensborg, Denmark. 'Poulpar038' was selected by the inventor as a single plant from the progeny of the hybridization in April 2003.

Asexual reproduction of 'Poulpar038' by cuttings and traditional budding was first done by Mogens N. Olesen in the nursery in Fredensborg, Denmark in 2003. This initial and other subsequent propagations conducted in controlled environments have demonstrated that the characteristics of 'Poulpar038' are true to type and are transmitted from one generation to the next.

BRIEF DECRIPTION OF THE DRAWING

The accompanying color illustration shows as true as is reasonably possible to obtain in color photographs of this type, the typical characteristics of the buds, flowers, leaves, and stems of 'Poulpar038'. Specifically illustrated in the drawing:

FIG. 1.1; Flower bud closed, and a partially open flower attached to stem, showing leaves and attachment of unopened flowers;

FIG. 1.2; Open flower viewed from above and lateral view;

FIG. 1.3; Sepals, receptacle, pedicel, and reproductive parts of the flower;

FIG. 1.4; Mature leaves (above) and juvenile leaves (below);

FIG. 1.5; Bare stem;

FIG. 1.6; Flower petals, detached.

DETAILED DESCRIPTION OF THE VARIETY

The following is a description of 'Poulpar038', as observed in its growth in glasshouses in Fredensborg, Denmark. Observed plants are 4 months of age and were cultivated in 10.5 cm pots. Color references are made using The Royal Horticultural Society (London, England) Colour Chart, 2001, except where common terms of color are used.

For a comparison, several physical characteristics of the rose variety 'Poulra024', illustrated and described in U.S. Plant Pat. No. 15,017, are compared to 'Poulpar038' in Chart 1.

CHART 1

| | 'Poulpar038' | 'Poulra024' |
|---|---|---|
| Petal count | 35 to 40 | 31 |
| Flower diameter | 65 to 75 mm | 45 to 50 mm |
| General tonality of flower color | Red-Purple N57 B | Red 52 C |

FLOWER AND FLOWER BUD

Blooming habit: Continuous.

Flower bud:

*Size.*—Upon opening, 25 mm in length from base of receptacle to end of bud. 9 mm in diameter.

*Bud form.*—Ovate.

*Bud color.*—As sepals unfold, petals are Red Group N57C with occasional streaks of White Group N155B.

*Sepals.*—Upper Surface: Color: Green Group 138B. The apecies are colored Yellow-Green Group 147A. Surface: Medium amount of pubescence. Lower Surface: Color: Yellow-Green Group 146A to 146B. Texture: Smooth with few stipitate glands. Shape: Apex: Cirrhose. Base: Flat at union with receptacle. Margins: Margins have strong foliaceous appendages on three of the five sepals. Stipitate glands are sparse. Size: 25 mm long by 8 to 10 mm wide.

*Receptacle.*—Surface Texture: Smooth. Shape: Urn-shaped. Size: 8 mm (h)×10 mm (w). Color: Yellow-Green Group 144B.

*Pedicel.*—Surface: Smooth with stipitate glands. Length: 20 mm average length. Diameter: 3 mm. Color: Yellow-Green Group 144B. Strength: Strong.

*Borne.*—Singularly and occasionally in clusters of 3 flower buds per stem.

Flower bloom:

*Fragrance.*—Light floral.

*Duration.*—As a pot plant, flowers last from 21 to 27 days. Petals do not fall cleanly away from plant.

*Size.*—Fully open diameter is 65–75 mm. Depth is 25 to 30 mm.

*Form.*—Petal arrangement is imbricated.

*Shape of flower, side view.*—Upon opening, the upper portion is flat. The lower portion is flat. After opening, the upper portion is flattened convex. The lower portion is slightly concave.

Petalage: There are normally 35 to 40 petals under normal conditions, 5 to 7 of which are petaloids.

Flower color:

*Upon opening, petals.*—Outermost petals: Upper Surface: Red-Purple Group N57A to N57 B. Lower Surface: Red-Purple Group N57C with occasional petal streaking of White Group N155B. Innermost petals: Upper Surface: Red-Purple Group N57A to N57 B. Lower Surface: Red-Purple Group N57C with occasional petal streaking of White Group N155B.

*Upon opening, basal petal spots.*—Upper Surface: Yellow Group 3C. Lower Surface: Yellow Group 3C to 4D.

*After opening, petals.*—Outermost and innermost petals: Upper Surface: Red-Purple Group N57A to N57 B. Lower Surface: Red-Purple Group N57C with occasional petal streaking of White Group N155B. Innermost petals: Upper Surface: Red-Purple Group N57A to N57 B. Lower Surface: Red-Purple Group N57C with occasional streaking of White Group N155B.

*After opening, basal petal spots.*—Upper Surface: Yellow Group 3C. Lower Surface: Yellow Group 3C to 4D.

General tonality: On open flower Red-Purple Group N57B. The color intonation changes slightly to a mixture of Red-Purple Group N57B and N57C as the flowers mature.

Petals:

*Petal reflex.*—Strong.

*Petal margin.*—Entire with occasional cleft in the margin. Weak undulations of the petal margin observed.

*Shape.*—Broad elliptical. Base: Acute. Apex: Rounded.

*Size.*—Outer petals: 35 mm (l)×32 mm (w). Inner petals: 26 mm (l)×26 mm (w).

*Thickness.*—Average.

*Texture.*—Smooth.

Petaloids:

*Size.*—Generally 18 mm long by 10 mm wide.

*Shape.*—Irregular.

*Color.*—Upper Surface: Red-Purple Group N57A to N57 B. Lower Surface: Red-Purple Group N57C with occasional streaking of White Group N155B.

Reproductive organs:

*Pollen.*—None observed.

*Anthers.*—Size: 2 to 3 mm long. Color: Yellow Group 4C. Quantity: 60 to 65.

*Filaments.*—Color: Yellow Group 8B to 8C. Length: Approximately 7 to 9 mm.

*Pistils.*—Length: Approximately 6 mm long. Quantity: 35 to 40.

*Stigmas.*—Level in location relative to the length of the filaments and the height of the anthers. Color: Greyed-Yellow Group 162C.

*Styles.*—Color: Red Group 53C.

*Seed formation.*—Not observed.

PLANT

Plant growth: Moderate upright and bushy. When grown as a 10.5 cm pot plant on its own roots, the average height of the plant itself is 15 to 18 cm and the average width is 15 cm.

Stems:

*Color.*—Young wood: Yellow-Green Group 144C. Older wood: Yellow-Green Group 146A.

*Internodal distance.*—20 mm.

*Length of stems.*—13 to 14 cm from the base of the stem to the flowering portion.

*Diameter.*—3 mm.

*Surface texture.*—Young wood: Smooth. Older wood: Smooth.

Thorns:

*Incidence.*—5 thorns per 10 cm of stem.

*Size.*—Normally 4 mm in length.

*Color.*—Juvenile thorns are Greyed-Yellow Group 144C and 144D. Mature thorns are Greyed-Yellow Group 144C and 144D.

*Shape.*—Upper side: Flat. Lower side: Flat.

Plant foliage: Normal number of leaflets on normal leaves in middle of the stem: 5 leaflets.

*Compound leaf size.*—85 mm (l)×60 mm (w).

*Quantity.*—4 to 5 leaves per 10 cm of stem.

*Color.*—Juvenile foliage: Upper Leaf Surface: Yellow-Green Group 144A to 144B. Lower Leaf Surface: Yellow-Green Group 144B to 144C. Mature foliage: Upper Leaf Surface: Yellow-Green Group 147A. Lower Leaf Surface: Yellow-Green Group 147B.

Plant leaves and leaflets:

*Stipules.*—Size: 8 to 10 mm in length. Shape: Linear, slightly broad based with outward extending apecies. Margins: Finely serrated. Color: Green Group 138 A.

*Petiole.*—Length: Normally 20 mm in length. Diameter: 1 to 1.5 mm. Upper Surface: Color: Yellow-Green Group 146B. Anthocyanin: Greyed-Orange Group 166A. Observations: Medium amount of stipitate glands observed on the upper surface. Lower Surface: Color: Yellow-Green Group 144B. Underneath: Few small prickles observed.

*Rachis.*—Size: Normally 25 mm in length. Upper Surface: Color: Yellow-Green Group 146B. Anthocyanin: Greyed-Orange Group 166A. Observations: Medium amount of stipitate glands observed. Lower Surface: Color: Yellow-Green Group 144B. Observations: Few small prickles.

*Leaflet.*—Edge: Doubly serrated. Size: 38 to 42 mm in length by 23 to 26 mm wide. General Shape: Ovate. Apex Shape: Acuminate. Base Shape: Obtuse to rounded. Texture: Rugose. Thickness: Average. Arrangement: Odd pinnate. Venation: Reticulate. Leaf Gloss: Very glossy finish.

Disease resistance: Average resistance to powdery and downy mildew, black spot, and *Botrytis* under normal growing conditions in Fredensborg, Denmark.

It is claimed:

1. A new and distinct variety of rose plant of the miniature class named 'Poulpar038', substantially as illustrated and described herein, due to its abundant, deep pink flowers, vigorous growth, compact habit, suitability for production from softwood cuttings in pots, and durable flowers and foliage that make the variety suitable for distribution in the floral industry.

* * * * *

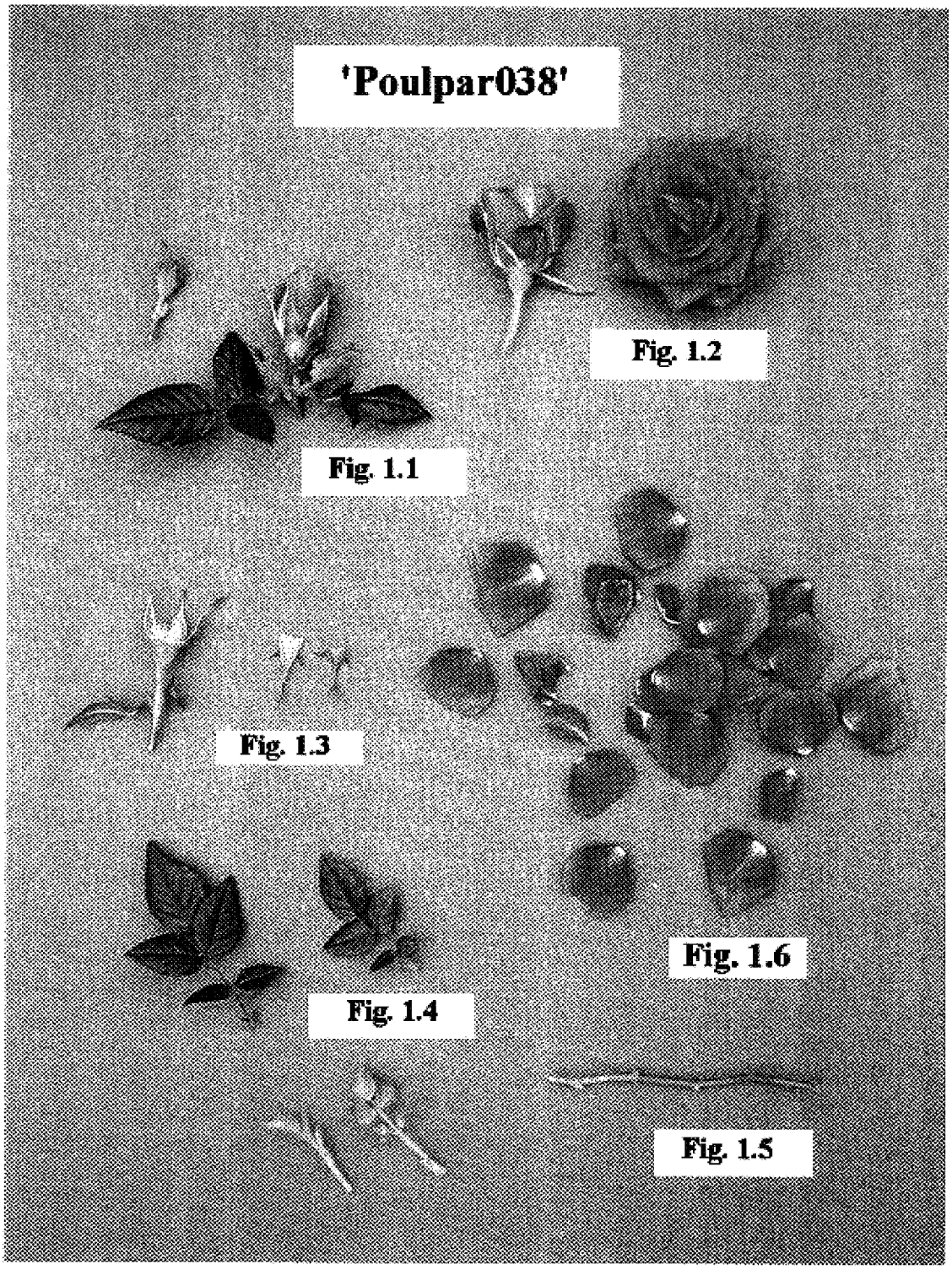
'Poulpar038'
Fig. 1.2
Fig. 1.1
Fig. 1.3
Fig. 1.6
Fig. 1.4
Fig. 1.5